(12) United States Patent
Mei et al.

(10) Patent No.: US 6,329,378 B1
(45) Date of Patent: Dec. 11, 2001

(54) HYDRAZONE, HYDRAZINE AND THIOSEMICARBAZONE DERIVATIVES AS ANTIFUNGAL AGENTS

(75) Inventors: Xiaodan Mei, Waltham; Peng Wang, Winchester; Andrei Caracoti, Waltham, all of MA (US); Pamela Mingo, Lake Forest, IL (US); Vincent Boyd, Pepperell, MA (US); Robert Murray, Watertown, MA (US); Nicholas J. Sisti, Pepperell, MA (US); Yi Bin Xiang, Acton, MA (US); Shuhao Zhu, Waltham, MA (US); C. Richard Wobbe, Lexington, MA (US); Daniel Moore, Medford, MA (US)

(73) Assignee: Anadys Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/501,758

(22) Filed: Feb. 10, 2000

Related U.S. Application Data

(60) Provisional application No. 06/119,387, filed on Feb. 10, 1999, and provisional application No. 60/141,117, filed on Jun. 25, 1999.

(51) Int. Cl.[7] ............... C07D 241/12; C07D 241/14; A61K 31/4965

(52) U.S. Cl. ............... 514/255.05; 544/405; 544/408; 544/409; 544/410; 514/255.06

(58) Field of Search .................. 544/405, 408, 544/409, 410; 514/255.05, 255.06

(56) References Cited

PUBLICATIONS

Konishi et al. Fungicidal activity of heteroaromatic aldehyde and ketone pyrimidinylhydrazones, Nippon Noyaku Gakkaishi, 14: 295–3000.*

Schilt et al. New chromogens of the ferroin type–IX 2–pyridyl and pyrazinylhydrazones of some pyridyl, pyrazinyl and pyridazinyl ketones and of isatin and phenylglyoxal, Talanta, 26: 373–6.*

* cited by examiner

Primary Examiner—Mukund J. Shah
Assistant Examiner—Hong Liu
(74) Attorney, Agent, or Firm—Darby & Darby

(57) ABSTRACT

Disclosed are pharmaceutical compositions comprising aryl and heteroaryl hydrazone, hydrazine and thiosemicarbazone derivatives of formulae I and II, and methods for using the compositions as antifungal agents. The invention also relates to novel aryl and heteroaryl hydrazone, hydrazine and thiosemicarbazone derivatives of formulae I and II, their preparation, to pharmaceutical compositions containing them, and to methods of using them to alleviate fungal infections.

11 Claims, No Drawings

HYDRAZONE, HYDRAZINE AND THIOSEMICARBAZONE DERIVATIVES AS ANTIFUNGAL AGENTS

This application claims priority under 35 U.S.C. §119(e) of U.S. provisional application Ser. No. 60/119,387, filed Feb. 10, 1999, and U.S. provisional application Ser. No. 60/141,117 filed Jun. 25, 1999.

FIELD OF THE INVENTION

The present invention is directed in part to novel aryl or heteroaryl substituted hydrazone, hydrazine and thiosemicarbazone compounds. The present invention is also directed to pharmaceutical compositions containing aryl and heteroaryl substituted hydrazone, hydrazine and thiosemicarbazone derivatives, and to methods of using them to alleviate fungal infections.

BACKGROUND OF THE INVENTION

New classes of antifungal agents are needed to address the growing resistance of fungi to present therapies. Desirable characteristics for new antifungal products include activity against drug resistant organisms, reduced propensity for resistance development, greater biological half-life in humans, reduced liability for allergic reactions, and broad spectrum anti-fungal activity.

Screening and counterscreening of a small molecule chemical library have produced a number of antifungal agents. Certain of these compounds are rapidly fungicidal, with broad spectrum antifungal activity in vitro. The aryl and heteroaryl hydrazone, hydrazine and thiosemicarbazone derivatives of the invention have been found to have potent antifungal activity.

OBJECTS OF THE INVENTION

One object of the present invention is to provide novel compounds which are capable of inhibiting fungal growth in a subject, including a human subject, an animal or in plants.

Another object of the invention is to provide compounds which are fungistatic or fungicidal against a broad spectrum of fungi.

A further object of the invention is to provide methods of inhibiting fungal growth using said novel compounds, either alone or in combination with synergistic agents.

A further object of the invention is to provide methods of treating subjects suffering from fungal infections using the novel compounds disclosed herein, either alone or in combination with synergistic agents such as amphotericin B.

SUMMARY OF THE INVENTION

The invention is directed to certain novel aryl or heteroaryl substituted hydrazone or hydrazine derivatives, comprising a compound of formula (I), pharmaceutical compositions comprising compounds of formula (I), and methods of treatment comprising the administration of compounds of formula (I). The invention is also directed to certain novel aryl or heteroaryl substituted thiosemicarbazone derivatives of formula (II), pharmaceutical compositions comprising compounds of formula (II), and methods of treatment comprising the administration of compounds of formula (II).

DETAILED DESCRIPTION OF THE INVENTION

In a first embodiment, the present invention is directed to novel hydrazone or hydrazine derivative compounds having the formula (I)

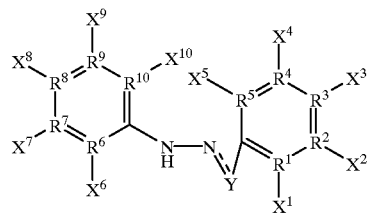

wherein

Y is CH when the dotted line leading from Y to N is present and represents a bond, or $CH_2$ when the dotted line leading from Y to N is absent;

$R^1$, $R^2$, $R^3$, $R^4$ and $R^5$ are each independently selected from the group consisting of carbon and nitrogen;

$X^1$, $X^2$, $X^3$, $X^4$ and $X^5$ is present only when said corresponding $R^1$, $R^2$, $R^3$, $R^4$ or $R^5$ is carbon, and (1)(a) $X^1$ is selected from the group consisting of ZH, wherein Z is O or S, or $NR^{21}R^{22}$, wherein $R^{21}$ and $R^{22}$ are independently selected from the group consisting of hydrogen, alkyl or acyl; and (b) $X^2$, $X^3$, $X^4$ and $X^5$ are independently selected from the group consisting of hydrogen, halogen, hydroxyl, alkyl, alkenyl, alkynyl, acyl, alkoxy, alkenyloxy, alkynyloxy, acyloxy, cyano, trifluoromethyl, nitro, aryl, heteroaryl, a non-aromatic heterocyclic group, a fused or polycyclic ring structure, N-alkyl amino, N-alkenyl amino, N-alkynyl amino, N-acyl amino, N,N-alkyl amino, N,N-alkenyl amino, N,N-alkynyl amino, N,N-acyl amino, thio, sulfonamide, and $SO_2$, or (2) $X^2$ and $X^3$, or $X^3$ and $X^4$, or $X^4$ and $X^5$, may together form a ring system which is fused to the compound of formula I; or (3) $X^2$, $X^3$, $X^4$, and $X^5$ are independently selected from the group consisting of (a) $C(O)NHQ^1Q^2$, wherein $Q^1$ is $C_{1-3}$ alkyl and $Q^2$ is aryl, heteroaryl or a non-aromatic heterocyclic group, wherein said aryl, heteroaryl or non-aromatic heterocyclic group is optionally substituted with hydroxyl, alkyl, alkoxy, carboxyl, or acyl; or (b) $C(O)Q^3$, wherein $Q^3$ is selected from the group consisting of hydrogen, OH, O—$C_{1-3}$ alkyl; or (c) $SO_2Q^4$, wherein $Q^4$ is aryl, heteroaryl or non-aromatic heterocyclic, wherein said aryl, heteroaryl or non-aromatic heterocyclic is optionally substituted with hydroxyl, alkyl, alkoxy, carboxyl or acyl; or (d) $OQ^5Q^6$, wherein $Q^5$ is $C_{1-3}$ alkyl and $Q^6$ is aryl, heteroaryl or a non-aromatic heterocyclic group, wherein said aryl, heteroaryl or non-aromatic heterocyclic group is optionally substituted with hydroxyl, alkyl, alkoxy, carboxyl, or acyl;

$R^6$, $R^7$, $R^8$, $R^9$ and $R^{10}$ are each independently selected from the group consisting of carbon and nitrogen;

$X^6$, $X^7$, $X^8$, $X^9$ and $X^{10}$ are present only when said corresponding $R^6$, $R^7$, $R^8$, $R^9$ or $R^{10}$ is carbon, and (1)(a) $X^6$, $X^7$, $X^8$, $X^9$ and $X^{10}$ is independently selected from the group consisting of hydrogen, halogen, hydroxyl, alkyl, alkenyl, alkynyl, acyl, alkoxy, alkenyloxy, alkynyloxy, acyloxy, cyano, trifluoromethyl, nitro, aryl, heteroaryl, a non-aromatic heterocyclic group, a fused or polycyclic ring structure, N-alkyl amino, N-alkenyl amino, N-alkynyl amino, N-acyl amino, N,N-alkyl amino, N,N-alkenyl amino, N,N-alkynyl amino, N,N-acyl amino, thio, sulfonamide, and sulfonyl; or (b) $X^6$ and $X^7$, or $X^7$ and $X^8$, or $X^8$ and $X^9$, or $X^9$ and $X^{10}$, may together form a ring system which is fused to the compound of formula I; or (2) $X^6$, $X^7$, $X^8$, $X^9$ and $X^{10}$ are independently selected from the group consisting of C(O)NHQ$^1$Q$^2$, wherein Q$^1$ is C$_{1-3}$ alkyl and Q$^2$ is aryl, heteroaryl or non-aromatic heterocyclic group, wherein said aryl, heteroaryl or non-aromatic heterocyclic group is optionally substituted with hydroxyl, alkyl, alkoxy, carboxyl, or acyl; or (3)(a) C(O)Q$^3$, wherein Q$^3$ is selected from the group consisting of hydrogen, OH, O—C$_{1-3}$ alkyl; or (b) SO$_2$Q$^4$, wherein Q$^4$ is aryl, heteroaryl or non-aromatic heterocyclic, wherein said aryl, heteroaryl or non-aromatic heterocyclic is optionally substituted with hydroxyl, alkyl, alkoxy, carboxyl or acyl; or (c) OQ$^5$Q$^6$, wherein Q$^5$ is C$_{1-3}$ alkyl and Q$^6$ is aryl, heteroaryl or a non-aromatic heterocyclic group, wherein said aryl, heteroaryl or non-aromatic heterocyclic group is optionally substituted with hydroxyl, alkyl, alkoxy, carboxyl, or acyl; and pharmaceutically acceptable salts thereof.

In further embodiments, the invention is directed to pharmaceutical compositions containing an aryl or heteroaryl hydrazone or hydrazine derivative of formula I, and a pharmaceutically acceptable carrier. The invention is also directed to methods of treating a subject suffering from a fungal disease or fungal infection, such as candidiasis, cutaneous or subcutaneous mycoses, as well as plant fungal infections, comprising administering an amount of the compound of formula (I).

In particular embodiments of the hydrazine and hydrazone derivatives, none of $X^2$–$X^{10}$ are bulky lipophilic groups, such as unsubstituted alkyl, alkenyl or alkynyl groups having 4 or more carbon atoms, unsubstituted aralkyl groups, such as benzyl, unsubstituted aryl groups, such as phenyl, SO$_2$Q$^4$ or OQ$^5$Q$^6$. In more preferred embodiments, none of $X^2$–$X^5$ are bulky lipophilic groups as described above.

In preferred embodiments of the hydrazine and hydrazone compounds, R$^1$ is C and X$^1$ is OH. In other preferred embodiments, R$^1$ is C and X$^1$ is OH, and at least three of R$^2$ to R$^5$ is carbon and at least one of X$^2$ to X$^5$ is a halogen. In still other preferred embodiments, R$^1$ is C and X$^1$ is OH, each of R$^2$ to R$^5$ is C, and at least one of X$^2$ to X$^5$ is COOH. More preferably, R$^1$ is C, X$^1$ is OH, each of R$^2$ to R$^5$ is C, and X$^4$ is COOH.

In other preferred embodiments of the hydrazine and hydrazone compounds of the invention, each of R$^6$ and R$^9$ is nitrogen, each of R$^7$, R$^8$ and R$^{10}$ is C, and X$^{10}$ is C$_{1-4}$ alkoxy, more preferably methoxy.

In a second embodiment, the invention is directed to novel thiosemicarbazone derivatives of the generic formula (II)

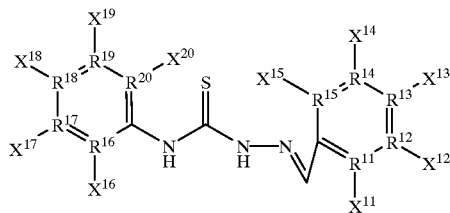

wherein R$^{11}$, R$^{12}$, R$^{13}$, R$^{14}$ and R$^{15}$ are each independently selected from the group consisting of carbon and nitrogen;

X$^{11}$, X$^{12}$, X$^{13}$, X$^{14}$ and X$^{15}$ is present only when said corresponding R$^{11}$, R$^{12}$, R$^{13}$, R$^{14}$ or R$^{15}$ is carbon, and (1)(a) X$^{11}$ is selected from the group consisting of ZH, wherein Z is O or S, or NR$^{23}$R$^{24}$, wherein R$^{23}$ and R$^{24}$ are independently selected from the group consisting of hydrogen, alkyl or acyl; and (b) X$^{12}$, X$^{13}$, X$^{14}$ and X$^{15}$ are independently selected from the group consisting of hydrogen, halogen, hydroxyl, alkyl, alkenyl, alkynyl, acyl, alkoxy, alkenyloxy, alkynyloxy, acyloxy, cyano, trifluoromethyl, nitro, aryl, heteroaryl, a non-aromatic heterocyclic group, a fused or polycyclic ring structure, N-alkyl amino, N-alkenyl amino, N-alkynyl amino, N-acyl amino, N,N-alkyl amino, N,N-alkenyl amino, N,N-alkynyl amino, N,N-acyl amino, thio, sulfonamide, and sulfonyl; or (2) X$^{12}$ and X$^{13}$, or X$^{13}$ and X$^{14}$, or X$^{14}$ and X$^{15}$, may together form a ring system which is fused to the compound of formula I; or (3) X$^{12}$, X$^{13}$, X$^{14}$ and X$^{15}$ are independently selected from the group consisting of (a) C(O)NHQ$^1$Q$^2$, wherein Q$^1$ is C$_{1-3}$ alkyl and Q$^2$ is aryl, heteroaryl or non-aromatic heterocyclic group, wherein said aryl, heteroaryl or non-aromatic heterocyclic group is optionally substituted with hydroxyl, alkyl, alkoxy, carboxyl, or acyl; or (b) C(O)Q$^3$, wherein Q$^3$ is selected from the group consisting of hydrogen, OH, O—C$_{1-3}$ alkyl; or (c) SO$_2$Q$^4$, wherein Q$^4$ is aryl, heteroaryl or non-aromatic heterocyclic, wherein said aryl, heteroaryl or non-aromatic heterocyclic is optionally substituted with hydroxyl, alkyl, alkoxy, carboxyl or acyl; or (d) OQ$^5$Q$^6$, wherein Q$^5$ is C$_{1-3}$ alkyl and Q$^6$ is aryl, heteroaryl or a non-aromatic heterocyclic group, wherein said aryl, heteroaryl or non-aromatic heterocyclic group is optionally substituted with hydroxyl, alkyl, alkoxy, carboxyl, or acyl;

R$^{16}$, R$^{17}$, R$^{18}$, R$^{19}$ and R$^{20}$ are each independently selected from the group consisting of carbon and nitrogen;

X$^{16}$, X$^{17}$, X$^{18}$, X$^{19}$ and X$^{20}$ are present only when said corresponding R$^{16}$, R$^{17}$, R$^{18}$, R$^{19}$ or R$^{20}$ is carbon, and (1)(a) each X$^{16}$, X$^{17}$, X$^{18}$, X$^{19}$ and X$^{20}$ is independently selected from the group consisting of hydrogen, halogen, hydroxyl, alkyl, alkenyl, alkynyl, acyl, alkoxy, alkenyloxy, alkynyloxy, acyloxy, cyano, trifluoromethyl, nitro, aryl, heteroaryl, a non-aromatic heterocyclic group, a fused or polycyclic ring structure, N-alkyl amino, N-alkenyl amino, N-alkynyl amino, N-acyl amino, N,N-alkyl amino, N,N-alkenyl amino, N,N-alkynyl amino, N,N-acyl amino, thio, sulfonamide, and sulfonyl; or (b) $X^{16}$ and $X^{17}$, or $X^{17}$ and $X^{18}$, or $X^{18}$ and $X^{19}$, or $X^{19}$ and $X^{20}$, may together form a ring system which is fused to the compound of formula II; or (c) $X^{16}$, $X^{17}$, $X^{18}$, $X^{19}$ or $X^{20}$ are independently selected from the group consisting of C(O)NHQ$^1$Q$^2$, wherein Q$^1$ is $C_{1-3}$ alkyl and Q$^2$ is aryl, heteroaryl or a non-aromatic heterocyclic group, wherein said aryl, heteroaryl or non-aromatic heterocyclic group is optionally substituted with hydroxyl, alkyl, alkoxy, carboxyl, or acyl; or (d) C(O)Q$^3$, wherein Q$^3$ is selected from the group consisting of hydrogen, OH, O—$C_{1-3}$ alkyl; or (e) SO$_2$Q$^4$, wherein Q$^4$ is aryl, heteroaryl or non-aromatic heterocyclic, wherein said aryl, heteroaryl or non-aromatic heterocyclic is optionally substituted with hydroxyl, alkyl, alkoxy, carboxyl or acyl; or (f) OQ$^5$Q$^6$, wherein Q$^5$ is $C_{1-3}$ alkyl and Q$^6$ is aryl, heteroaryl or a non-aromatic heterocyclic group, wherein said aryl, heteroaryl or non-aromatic heterocyclic group is optionally substituted with hydroxyl, alkyl, alkoxy, carboxyl, or acyl; and pharmaceutically acceptable salts thereof In further embodiments, the invention is directed to pharmaceutical compositions containing thiosemicarbazone derivatives of formula (II), and a pharmaceutically acceptable carrier. The invention is also directed to methods of treating a subject suffering from a fungal disease or fungal infection, such as candidiasis, cutaneous or subcutaneous mycoses, as well as plant fungal infections, comprising administering an amount of the compound of formula (II).

In preferred embodiments of the thiosemicarbazone derivatives, at least one of $X^{16}$ to $X^{20}$ is halogen, $C_{1-4}$ alkyl (more preferably methyl), $C_{1-4}$ alkoxy (more preferably methoxy), CF$_3$ or C(O)$C_{1-4}$ alkyl (more preferably acetyl). More preferably one of $X^{16}$–$X^{20}$ is from the group described above and each of the others are hydrogen.

In other preferred embodiments, R$^4$ is C and X$^4$ is a bulky lipophilic group, for example, alkyl, alkenyl or alkynyl having 4 or more carbon atoms; aryl groups such as phenyl; aralkyl groups such as benzyl; alkoxy groups having 4 or more carbon atoms; aralkoxy; SO$_2$Q$^4$ or OQ$^5$Q$^6$.

In other preferred embodiments, each of R$^{10}$ to R$^{15}$ is carbon, $X^{11}$ is hydroxyl and at least one of $X^{12}$ to $X^{15}$ is a halogen, more preferably chloro.

In other preferred embodiments, each of R$^{15}$ to R$^{20}$ is carbon, and at least one of $X^{16}$ to $X^{20}$ is halogen or CF$_3$.

When any aryl or heteroaryl substituted hydrazone, hydrazine or thiosemicarbazone derivative compound or isostere thereof disclosed herein is substituted by an amino, alkyl- or aryl- or heteroaryl-amino, or dialkyl- or alkylaryl- or alkylheteroaryl-amino, or diaryl- or diheteroarylamino, an acid addition salt thereof may be formed by methods known to one of skill in the art. Such salts encompass all pharmaceutically acceptable salts, including salts prepared from a mineral acid or an organic acid. Examples of useful mineral acids for this purpose are hydrochloric acid, hydrobromic acid, hydroiodic acid, phosphoric acid, sulfuric acid, and the like. Examples of organic acids used to form addition salts include p-toluenesulfonic acid, methanesulfonic acid, oxalic acid, succinic acid, citric acid, malic acid, benzoic acid, carbonic acid, and the like.

DEFINITIONS

As used herein, the term "aryl" means an aromatic carbocyclic ring system having a single radical containing about 6 to about 10 carbon atoms. An aryl group may be a fused or polycyclic ring system. Exemplary aryl groups include phenyl and napthyl.

The term "substituted aryl" refers to an aryl group substituted with one, two or three substituents independently selected from halo, hydroxy, protected hydroxy, cyano, nitro, alkyl, alkoxy, carboxy, protected carboxy, carbamoylmethyl, hydroxymethyl, amino, aminomethyl, trifluoromethyl, N-methylsulfonylamino, and the like.

As used herein, the term "ring system" refers to an aromatic or non-aromatic carbocyclic compound, in which one or more of the ring carbon atoms may be replaced by a heteroatom, such as nitrogen, oxygen or sulfur. The ring system may be optionally substituted by one or more halogens, $C_1$ to $C_{12}$ alkyl, aryl, vinyl, alkyl(aryl), vinyl(aryl) and nitro groups.

As used herein, the term "fused ring system" refers to ring systems wherein at least two adjacent carbon centers join one or more cyclic structures. A fused ring system as used herein may be aromatic or non-aromatic, or may be composed of separate aromatic and non-aromatic moieties. Exemplary carbocyclic fused ring systems are represented by the formulae:

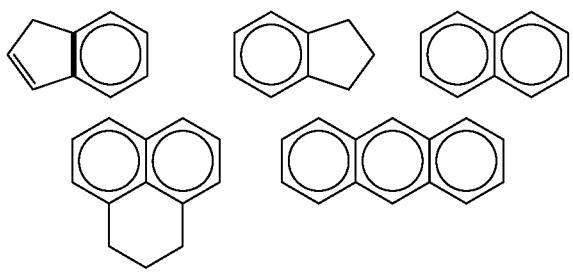

Exemplary fused ring systems in which one or more of the ring carbon atoms is replaced by a heteroatom include the following:

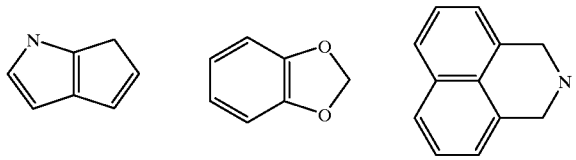

As used herein, the term "polycyclic ring system" refers to ring systems having two or more cyclic compounds bonded in tandem. A polycyclic ring system as used herein may be aromatic or non-aromatic, or may be composed of separate aromatic and non-aromatic moieties. An exemplary carbocyclic polycyclic ring system is represented by the formula

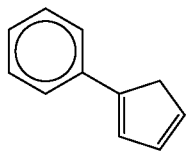

An exemplary polycyclic ring system in which one or more of the ring carbon atoms is replaced by a heteroatom include the following:

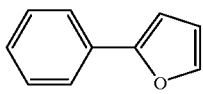

Additionally, fused or polycyclic ring systems may optionally be substituted by one or more halogens, $C_1$ to $C_{12}$ alkyl, aryl, vinyl, alkyl(aryl), vinyl(aryl) and nitro groups.

As used herein, the term "heteroaryl" means an about 5 to 10-membered aromatic monocyclic or fused or polycyclic ring system having a single radical in which one or more of the atoms in the ring system is other than carbon, for example, nitrogen, oxygen or sulfur. An exemplary heteroaryl group is pyridine. An exemplary fused or polycyclic heteroaryl group is indole.

The term "substituted heteroaryl" refers to a heteroaryl group substituted with one, two or three substituents independently selected from halo, hydroxy, protected hydroxy, cyano, nitro, alkyl, alkoxy, carboxy, protected carboxy, carbamoylmethyl, hydroxymethyl, amino, aminomethyl, trifluoromethyl, N-methylsulfonylamino, and the like.

The term "protected hydroxy" or "protected carboxy" refers to the use of a "hydroxy protecting group," a substituent of a hydroxy group that is commonly employed to block or protect the hydroxy functionality (including the hydroxy functionality of a carboxyl group) while reactions are carried out on other functional groups on the compound. Examples of such hydroxy protecting groups include tetrahydropyranyl, 2-methoxyprop-2-yl, 1-ethoxyeth-1-yl, methoxymethyl, β-methoxyethoxymethyl, methylthiomethyl, t-butyl, t-amyl, trityl, benzyl, trimethylsilyl, and the like.

The term "protected amino" refers to the use of an "amino protecting group," a substituent of an amino group that is commonly employed to block or protect the amino functionality or reactions that are carried out on the compounds.

As used herein, the term "heterocyclyl" or "heterocyclic" means an aromatic or non-aromatic about 5 to about 10-membered monocyclic or fused or polycyclic ring system in which one or more of the atoms in the ring system is other than carbon, for example, nitrogen, oxygen or sulfur. A heterocyclyl group may be a fused or polycyclic ring system. Exemplary heterocyclyl groups include piperidine, morpholino, and azepanyl.

As used herein, the term "alkyl" refers to a straight or branched chain alkyl having up to about twelve carbon atoms, and preferably (in some embodiments) refers to lower alkyl groups having 1 to 5 carbon atoms. Typical lower alkyl groups include methyl, ethyl, propyl, isopropyl, butyl, sec-butyl, t-butyl and pentyl. The term "substituted alkyl" refers to substitution of one or more hydrogen atoms of the alkyl moiety with a substituent independently selected from halo, hydroxy, protected hydroxy, amino, protected amino, acyloxy, nitro, carboxy, protected carboxy, carbamyl, aryl, substituted aryl or alkoxy.

The term "alkenyl" refers to a straight or branched chain hydrocarbon having a single radical and at least one carbon to carbon double bond, in some embodiments preferably having up to about 12 carbon atoms. More preferred alkenyl groups are those having 1 to 5 carbon atoms. The term "substituted alkenyl" refers to substitution of one or more hydrogen atoms of the alkenyl moiety with a substituent independently selected from halo, hydroxy, protected hydroxy, amino, protected amino, acyloxy, nitro, carboxy, protected carboxy, carbamyl, aryl, substituted aryl or alkoxy.

The term "alkynyl" as used herein includes straight chained or branched chain hydrocarbon groups having a single radical and at least one carbon to carbon triple bond, in some embodiments preferably having up to about 12 carbon atoms. More preferred alkynyl groups are those having 1 to 5 carbon atoms. The term "substituted alkynyl" as used herein refers to substitution of one or more hydrogen atoms of the alkynyl moiety with a substituent independently selected from halo, hydroxy, protected hydroxy, amino, protected amino, acyloxy, nitro, carboxy, protected carboxy, carbamyl, aryl, substituted aryl or alkoxy.

The term "alkoxy" is a group —OR, wherein R is a straight or branched chain alkyl group, in some embodiments preferably having up to about twelve carbon atoms, more preferably having from 1 to 5 carbon atoms. Exemplary preferred alkoxy groups include methoxy, ethoxy, propoxy, butoxy, sec-butoxy and pentoxy. Other exemplary alkoxy groups contemplated by the invention include heptoxy, octyloxy, and the like.

The term "alkenyloxy" is a group —OR, wherein R is a straight or branched chain alkenyl group, in some embodiments preferably having up to twelve carbon atoms. More preferred alkenyloxy groups are those having 1 to 5 carbon atoms.

The term "alkynyloxy" is a group —OR, wherein R is a straight or branched chain alkynyl group, in some embodiments preferably having up to twelve carbon atoms. More preferred alkynyloxy groups are those having 1 to 5 carbon atoms.

The term "acyl" is a group RC(=O)—, wherein R is an alkyl, alkenyl, alkynyl, aryl, amino, amino alkyl, amino alkenyl, amino alkynyl, amino aryl, oxy, oxyalkyl, oxyalkenyl, oxyalkynyl, or oxy aryl group. Preferred alkyl, alkenyl and alkynyl R groups (in some embodiments) are those having up to twelve carbon atoms, more preferably 1 to 5 carbon atoms. Exemplary aryl R groups are phenyl and napthyl.

The term "acyloxy" is a group O—R, wherein R is an acyl group, as described above.

The term "sulfonamide" refers to the group $SO_2NH$—.

The term "sulfonyl" refers to the group $SO_2$—.

The term "halo" or "halogen" encompasses fluorine, chlorine, bromine and iodine.

The term "N,N-alkyl amino" refers to an N-alkyl amino group in which the N atom of the amino group is also substituted with a substituent selected from the group consisting of alkyl, alkenyl, alkynyl or acyl. Preferred alkyl, alkenyl, alkynyl or acyl groups (in some embodiments) are those having up to twelve carbon atoms, more preferably from 1 to 5 carbon atoms.

The term "N, N-alkenyl amino" refers to an N-alkenyl amino group in which the N atom of the amino group is also substituted with a substituent selected from the group consisting of alkyl, alkenyl, alkynyl or acyl. Preferred alkyl, alkenyl, alkynyl or acyl groups (in some embodiments) are those having up to twelve carbon atoms, more preferably from 1 to 5 carbon atoms.

The term "N,N-alkynyl amino" refers to an N-alkynyl amino group in which the N atom of the amino group is also substituted with a substituent selected from the group consisting of alkyl, alkenyl, alkynyl or acyl. Preferred alkyl, alkenyl, alkynyl or acyl groups (in some embodiments) are those having up to twelve carbon atoms, more preferably from 1 to 5 carbon atoms.

The term "N,N-acyl" refers to an N-acyl amino group in which the N atom of the amino group is also substituted with a substituent selected from the group consisting of alkyl, alkenyl, alkynyl or acyl. Preferred alkyl, alkenyl, alkynyl or acyl groups (in some embodiments) are those having up to twelve carbon atoms, more preferably from 1 to 5 carbon atoms.

The term N-substituted amino refers to an amino group in which the N atom of the amino group is substituted with a substituent selected from the group consisting of an alkyl, alkenyl, alkynyl, acyl, amino or substituted amino.

The term N,N-substituted amino refers to an amino group in which the N atom of the amino group is twice substituted with substituents independently selected from the group consisting of an alkyl, alkenyl, alkynyl, acyl, amino or substituted amino.

Exemplary Embodiments

Aryl and Heteroaryl Substituted Hydrazone Derivatives

Particular aryl hydrazone derivatives of formula (I) include the following:

3,5-dichloro-2-hydroxybenzaldehyde-N-(3-methoxy-2-pyrazinyl) hydrazone (1):

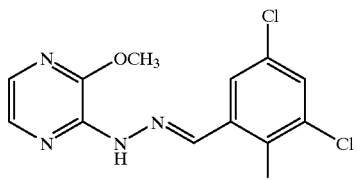

5-chloro-2-hydroxybenzaldehyde-N-(3-methoxy-2-pyrazinyl) hydrazone (2):

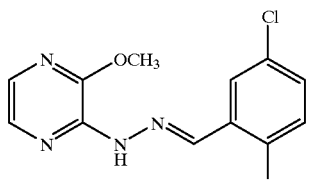

3-fluoro-2-hydroxybenzaldehyde-N-(3-methoxy-2-pyrazinyl) hydrazone (3):

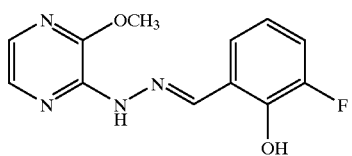

2-hydroxybenzaldehyde-N-(3-methoxy-2-pyrazinyl) hydrazone (4):

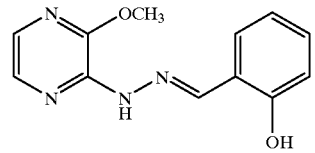

4,6-dimethoxy-2-hydroxybenzaldehyde-N-(3-methoxy-2-pyrazinyl) hydrazone (5):

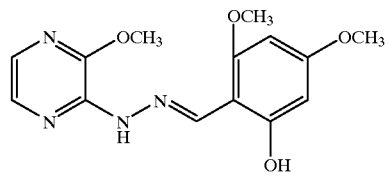

2,3-dihydroxybenzaldehyde-N-(3-methoxy-2-pyrazinyl) hydrazone (6):

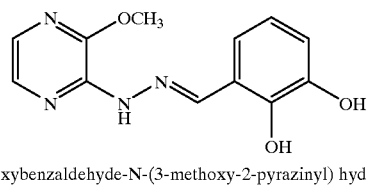

2,4-dihydroxybenzaldehyde-N-(3-methoxy-2-pyrazinyl) hydrazone (7):

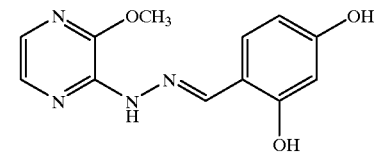

2,3.4-trihydroxybenzaldehyde-N-(3-methoxy-2-pyrazinyl) hydrazone (8):

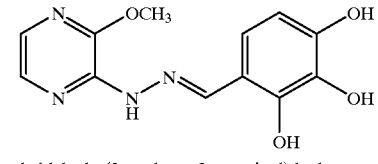

2-quinolinecarbaldehyde-(3-methoxy-2-pyrazinyl) hydrazone (9):

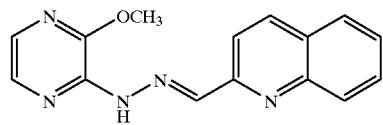

2-pyridinecarbaldehyde-N-(3-methoxy-2-pyrazinyl) hydrazone (10)

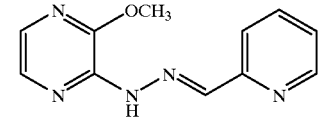

Additional exemplary hydrazone derivatives include the following:
3-ethoxy-2-hydroxybenzaldehyde-N-(3-methoxy-2-pyrazinyl)hydrazone (11);
2-hydroxy-3-nitrobenzaldehyde-N-(3-methoxy-2-pyrazinyl)hydrazone (12);
2-hydroxy-4-methoxybenzaldehyde-N-(3-methoxy-2-pyrazinyl)hydrazone (13);
5-bromo-2-hydroxy-3-methoxybenzaldehyde-N-(3-methoxy-2-pyrazinyl)hydrazone (14);
6-bromo-2-hydroxy-3-methoxybenzaldehyde-N-(3-methoxy-2-pyrazinyl)hydrazone (15);

3,5-dichloro-2-hydroxybenzaldehyde-N-(3-chloro-2-pyrazinyl)hydrazine (16);
3-carboxyl-2-hydroxybenzaldehyde-N-(3-methoxy-2-phenyl)hydrazine (17);
5-carboxyl-2-hydroxybenzaldehyde-N-phenyl hydrazone (18);
2-hydroxybenzaldehyde-N-phenyl hydrazone (19);
5-carboxyl-2-hydroxybenzaldehyde-N-3-nitro-phenyl hydrazone (20);
5-carboxyl-2-hydroxybenzaldehyde-N-2-trifluoromethyloxy-phenyl hydrazone (21);
5-carboxyl-2-hydroxybenzaldehyde-N-2-carboxyl-phenyl hydrazone (22);
5-carboxyl-2-hydroxybenzaldehyde-N-3-fluorophenyl hydrazone (23);
5-carboxyl-2-hydroxybenzaldehyde-N-2-fluoro-phenyl hydrazone (24);
5-carboxyl-2-hydroxybenzaldehyde-N-2-bromophenyl hydrazone (25);
5-carboxyl-2-hydroxybenzaldehyde-N-2-chlorophenyl hydrazone (26);
5-carboxyl-2-hydroxybenzaldehyde-N-3-methyl-phenyl hydrazone (27);
5-carboxyl-2-hydroxybenzaldehyde-N-2-methoxy-phenyl hydrazone (28);
5-carboxyl-2-hydroxybenzaldehyde-N-3-chloro-2-methyl-phenyl hydrazone (29); and
5-carboxyl-2-hydroxybenzaldehyde-N-3-chloro-phenyl hydrazone (30).

The following table shows the substitution pattern of the exemplary hydrazone compounds, wherein each of $R^2$–$R^5$ is carbon; each of $X^2$–$X^5$ is hydrogen unless otherwise indicated below; each of $R^7$, $R^8$ and $R^{10}$ is carbon; and each of $X^6$–$X^{10}$ is hydrogen unless otherwise indicated below.

| Compound | $R^1$ | $X^1$ | $X^2$–$X^5$ | $R^6$ | $R^9$ | $X^6$–$X^{10}$ |
|---|---|---|---|---|---|---|
| (1) | C | OH | $X^3$ = Cl, $X^4$ = Cl | N | N | $X^{10}$ = $OCH_3$ |
| (2) | C | OH | $X^4$ = Cl | N | N | $X^{10}$ = $OCH_3$ |
| (3) | C | OH | $X^2$ = F | N | N | $X^{10}$ = $OCH_3$ |
| (4) | C | OH | — | N | N | $X^{10}$ = $OCH_3$ |
| (5) | C | OH | $X^4$, $X^6$ = $OCH_3$ | N | N | $X^{10}$ = $OCH_3$ |
| (6) | C | OH | $X^2$ = OH | N | N | $X^{10}$ = $OCH_3$ |
| (7) | C | OH | $X^3$ = OH | N | N | $X^{10}$ = $OCH_3$ |
| (8) | C | OH | $X^3$, $X^4$ = OH | N | N | $X^{10}$ = $OCH_3$ |
| (9) | N | — | fused ring | N | N | $X^{10}$ = $OCH_3$ |
| (10) | N | — | — | N | N | $X^{10}$ = $OCH_3$ |
| (11) | C | OH | $X^2$ = $OCH_2CH_3$ | N | N | $X^{10}$ = $OCH_3$ |
| (12) | C | OH | $X^2$ = $NO_2$ | N | N | $X^{10}$ = $OCH_3$ |
| (13) | C | OH | $X^3$ = $OCH_3$ | N | N | $X^{10}$ = $OCH_3$ |
| (14) | C | OH | $X^2$ = $OCH_3$, $X^4$ = Br | N | N | $X^{10}$ = $OCH_3$ |
| (15) | C | OH | $X^2$ = $OCH_3$, $X^5$ = $OCH_3$ | N | N | $X^{10}$ = $OCH_3$ |
| (16) | C | OH | — | N | N | $X^{10}$ = $OCH_3$ |
| (17) | C | OH | $X^2$ = COOH | N | N | $X^{10}$ = $OCH_3$ |
| (18) | C | OH | $X^4$ = COOH | C | C | — |
| (19) | C | OH | — | C | C | — |
| (20) | C | OH | $X^4$ = COOH | C | C | $X^9$ = $NO_2$ |
| (21) | C | OH | $X^4$ = COOH | C | C | $X^{10}$ = $OCF_3$ |
| (22) | C | OH | $X^4$ = COOH | C | C | $X^{10}$ = COOH |
| (23) | C | OH | $X^4$ = COOH | C | C | $X^9$ = F |
| (24) | C | OH | $X^4$ = COOH | C | C | $X^{10}$ = F |
| (25) | C | OH | $X^4$ = COOH | C | C | $X^{10}$ = Br |
| (26) | C | OH | $X^4$ = COOH | C | C | $X^{10}$ = Cl |
| (27) | C | OH | $X^4$ = COOH | C | C | $X^9$ = $CH_3$ |
| (28) | C | OH | $X^4$ = COOH | C | C | $X^{10}$ = $OCH_3$ |
| (29) | C | OH | $X^4$ = COOH | C | C | $X^9$ = Cl, $X^{10}$ = $CH_3$ |
| (30) | C | OH | $X^4$ = COOH | C | C | $X^7$ = Cl |

A general procedure for the preparation of aryl hydrazones of the formula (I) is described herein. Commencing from an optionally substituted aryl halide, preferably an aryl fluoro derivative (See Kaufmann, T. et al., *Chem. Ber.* 96: 3159 (1963); Pfannstiel, K., et al, *Ber. Dtsch. Chem. Ges.* 75: 1096 (1942); *Chem Abstr.:* 4392 (1943); Mann, F. G. et al, *J. Chem. Soc.:* 3830 (1959); Carmi, A., et al, *J. Org. Chem.* 25: 44 (1960); Gregory, H., et al *J. Chem. Soc.:* 2546 (1949); Katz, L., *J. Am. Chem. Soc.* 73: 4007 (1951), all of which are incorporated by reference) dissolved in a suitable solvent, such as an ethereal solvent or alcoholic solvent, hydrazine is added. The resulting aryl hydrazine is then reacted with a suitably substituted aryl or heteroaryl aldehyde available from Aldrich Chemical Co. or Lancaster Synthesis, or by methods known to one of ordinary skill in the art (see March, *Advanced Organic Chemistry,* 3rd ed. 1985, which is hereby incorporated by reference) in the presence of an organic acid, preferably acetic acid, to afford the heteroaryl or aryl hydrazines.

Aryl and Heteroaryl Substituted Hydrazones Derivatives

An exemplary hydrazine compound is (32) 2-hydroxybenzaldehyde-N-phenyl hydrazine:

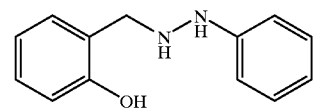

Other exemplary hydrazine compounds are the following:
(33) 2-hydroxybenzaldehyde-N-(3-methoxy-2-pyrazinyl) hydrazine; and
(34) 2-pyridyl-benzaldehyde-N-(3-methoxy-2-pyrazinyl) hydrazine.

The following table sets forth the substitution pattern of the exemplary hydrazine compounds of the invention, wherein each of $R^2$ to $R^5$ is carbon; each of $X^2$ to $X^5$ is hydrogen; each of $R^7$, $R^8$ and $R^{10}$ is C; and each of $X^6$ to $X^{10}$ is hydrogen unless otherwise indicated below.

| Compound | $R^1$ | $X^1$ | $R^6$ | $R^9$ | $X^6$–$X^{10}$ |
|---|---|---|---|---|---|
| (32) | C | OH | C | C | — |
| (33) | C | OH | N | N | $X^{10}$ = $OCH_3$ |
| (34) | N | — | N | N | $X^{10}$ = $OCH_3$ |

A general procedure for the preparation of heteroaryl hydrazines of the formula I is described herein. Commencing from an optionally substituted heteroaryl halide dissolved in a suitable alcoholic solvent, preferably ethanol, hydrazine is added. The resulting solution is then heated for a period of time to form the heteroaryl hydrazine. The resulting heteroaryl hydrazine is then reacted with a suitably substituted aryl or heteroaryl aldehyde in an ethereal solvent, preferably tetrahydrofuran, in the presence of an organic acid, preferably acetic acid, to afford the heteroaryl hydrazines.

Aryl and Heteroaryl Substituted Thiosemicarbazone Derivatives

Particular thiosemicarbazone derivatives of formula (II) include the following:

N-[3,5 bis(trifluoromethyl)phenyl]-2-[(E)-3,5-dichloro-2-hydroxyphenyl)
methylidene]-1-hydrazonecarbothioamide (35):

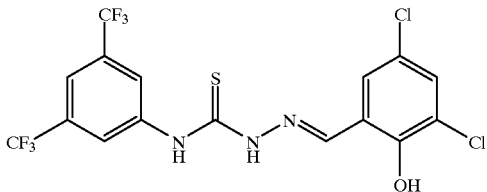

N-[4-fluorophenyl]-2-[(E)-(3,5-dichloro-2-hydroxyphenyl)
methylidene]-1-hydrazonecarbothioamide (36):

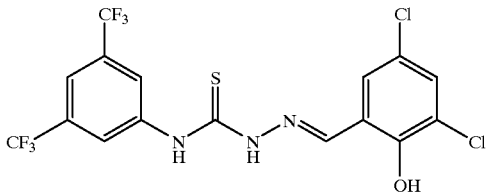

N-[3,5-bis(trifluoromethyl)phenyl]-2-[(E)-2-pyridinyl
methylidene]-1-hydrazonecarbothioamide (37):

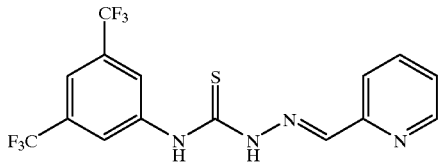

N-[3-(trifluoromethyl)phenyl]-2-[(E)-2-pyridinyl
methylidene]-1-hydrazonecarbothioamide (38):

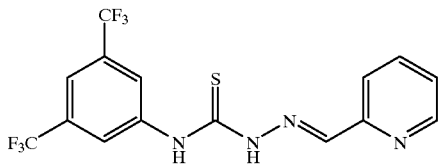

N-[4-fluorophenyl]-2-[(E)-2-pyridinyl
methylidene-1-hydrazonecarbothioamide (39):

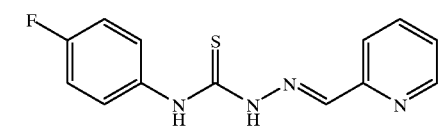

N-[3-fluorophenyl]-2-[(E)-(2-hydroxyphenyl
methylidene]-1-hydrazonecarbothioamide (40):

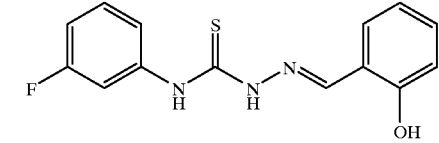

Other exemplary thiosemicarbazone derivatives are the following:

N-3-phenyl-2-[(E)-(2-pyridinyl methylidene]-1-hydrazone carbothioamide (41);

N-[(3-trifluoromethyl)phenyl)]-2-[(E)-(4-benzyloxy-2-hydroxyphenyl)methylidene]-1-hydrazonecarbothioamide (42);

N-[(3-trifluoromethyl)phenyl)]-2-[(E)-(4-carbomethoxy-benzyloxy-2-hydroxyphenyl)methylidene]-1-hydrazonecarbothiamide (43);

N-[(3-trifluoromethyl)phenyl)]-2-[(E)-(4-allyl-phenyl)-benzyloxy-2-hydroxyphenyl)methylidene]-1-hydrazonecarbothiamide (44);

N-[(4-chloro-phenyl)]-2-[(E)-(4-benzyloxy-2-hydroxyphenyl)methylidene]-1-hydrazonecarbothiamide (45);

N-[(4-chloro-phenyl)]-2-[(E)-(4-(carbomethoxy-benzyloxy-2-hydroxyphenyl)methylidene]-1-hydrazonecarbothiamide (46);

N-[(4-chloro-phenyl)]-2-[(E)-(4-carboxyl-benzyloxy-2-hydroxyphenyl)methylidene]-1-hydrazonecarbothiamide (47);

N-[(3-trifluoromethyl)phenyl)]-2-[(E)-(4-diethylamino-2-hydroxyphenyl)methylidene]-1-hydrazonecarbothiamide (48);

N-[(3-trifluoromethyl)phenyl)]-2-[(E)-(4-morpholino-2-hydroxyphenyl)methylidene]-1-hydrazonecarbothiamide (49);

N-[(3,5-dimehtyl)phenyl)]-2-[(E)-(4-benzyloxy-2-hydroxyphenyl)methylidene]-1-hydrazonecarbothiamide (50);

N-[(sulfonyl-N-piperidine)phenyl)]-2-[(E)-(4-benzyloxy-2-hydroxyphenyl)methylidene]-1-hydrazonecarbothiamide (51); and N-[(4-dimethylamino)sulfonyl-N-piperidyl)phenyl)]-2-[(E)-(4-benzyloxy-2-hydroxyphenyl)methylidene]-1-hydrazonecarbothiamide (52).

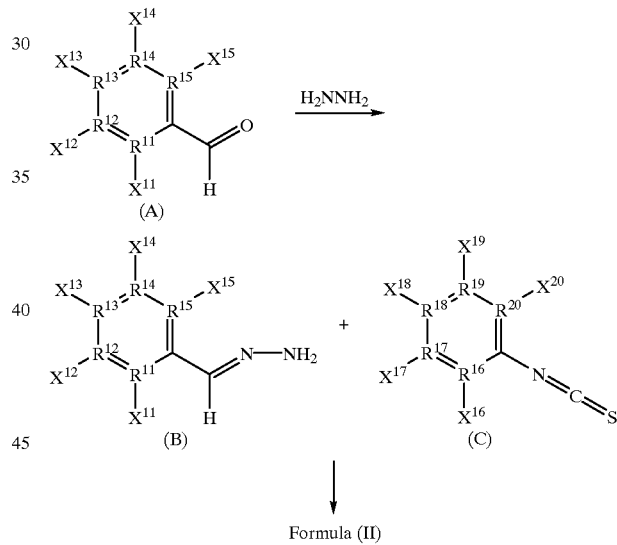

Formula (II)

This semicarbazone derivative of the generic formula (II) may be synthesized in the following manner.

Aromatic aldehydes of the form (A) which are readily available from Aldrich Chemical Company (Milwaukee, Wis.) and Lancaster Synthsis (Lancaster, Pa.) or can be synthesized using methods known to one of ordinary skill in the art (See March, op. cit.), are reacted with hydrazine to form the hydrazones of the form (B). The hydrazones are then reacted with the thioisocyanates of the form (C) which are readily available from Aldrich Chemical Co. or Lancaster Synthesis, or can be synthesized using methods known to one of ordinary skill in the art (See March, *Advanced Organic Chemistry*, 3rd Edition 1985), to form compounds of the formula II as described herein.

The following table describes exemplary thiosemicarbazone compounds, wherein each of $R^{12}$ to $R^{15}$ is carbon; each of $X^{12}$ to $X^{15}$ is hydrogen unless otherwise indicated below;

each of $R^{16}$ to $R^{20}$ is carbon; and each of $X^{16}$ to $X^{20}$ is hydrogen unless otherwise indicated below.

| Compound | $R^{11}$ | $X^{11}$ | $X^{12}$–$X^{15}$ | $X^{16}$–$X^{20}$ |
|---|---|---|---|---|
| (35) | C | OH | $X^{12}$ = Cl, $X^{14}$ = Cl | $X^{17}$, $X^{19}$ = $CF_3$ |
| (36) | C | OH | $X^{12}$ = Cl, $X^{14}$ = Cl | $X^{17}$, $X^{19}$ = $CF_3$ |
| (37) | N | — | — | $X^{17}$, $X^{19}$ = $CF_3$ |
| (38) | N | — | — | $X^{17}$, $X^{19}$ = $CF_3$ |
| (39) | N | — | — | $X^{18}$ = F |
| (40) | C | OH | — | $X^{17}$ = F |
| (41) | N | — | — | — |
| (42) | C | OH | $X^{13}$ = benzyloxy | $X^{17}$ = $CF_3$ |
| (43) | C | OH | $X^{13}$ = 4-carbomethoxy-benzyloxy | $X^{17}$ = $CF_3$ |
| (44) | C | OH | $X^{13}$ = 4-(E-)-allyl-phenyl-benzyloxy | $X^{17}$ = $CF_3$ |
| (45) | C | OH | $X^{13}$ = benzyloxy | $X^{18}$ = Cl |
| (46) | C | OH | $X^{13}$ = 4-carbomethoxy-benzyloxy | $X^{18}$ = Cl |
| (47) | C | OH | $X^{13}$ = 4-carboxy-benzyloxy | $X^{18}$ = Cl |
| (48) | C | OH | $X^{13}$ = N(Et)$_2$ | $X^{17}$ = $CF_3$ |
| (49) | C | OH | $X^{13}$ = N-morpholino | $X^{17}$ = $CF_3$ |
| (50) | C | OH | $X^{13}$ = O-benzyl | N-(3,5-dimethyl)-morpholino sulfonyl-N-piperidine |
| (51) | C | OH | $X^{13}$ = benzyloxy | |
| (52) | C | OH | $X^{13}$ = benzyloxy | $X^{18}$ = N(CH$_3$)$_2$ |

Detailed Description of The Exemplary Embodiments Synthetic Examples

The following is a chemical process for the efficient production of substituted aryl and heteroaryl aldehyde-N-(3-methoxy-2-pyrazinyl)hydrazones which are useful as antifungal agents.

A. Production of 2-Methoxy-3-Chloro Pyrazine From 2,3-Dichloropyrazine.

Commercially available 2,3 dichloropyrazine was dissolved in a suitable amount of methanol to which was added a slight excess of an alkali methoxide, preferably 1.05 equiv. of sodium methoxide. The mixture was then stirred for a period of 1–24 hr, preferably 7 hr, after which time the solution was neutralized with solid ammonium chloride, the solvent removed in vacuo, the residue taken up in an organic solvent chosen from a group consisting of diethyl ether, ethyl acetate, and methylene chloride, preferably methylene chloride, and filtered to remove unwanted salts. The filtrate was reduced in vacuo to afford 2-methoxy-3-chloropyrazine as white crystals which were used without further purification.

B. Production of 2-Methoxy-3-Hydrazinyl Pyrazine from 2-Methoxy-3-Chloro Pyrazine.

2-Methoxy-3-chloro pyrazine was dissolved in a suitable amount of an alcoholic solvent, preferably ethanol, to which was added hydrazone. The reaction mixture was then allowed to stir for a period of 1–24 hrs, preferably 12 hrs, after which time the reaction mixture was filtered and the collected crystals washed with hexane to afford 2-methoxy-3-hydrazinyl-pyrazine which was used without further purification.

Hydrazine derivatives of the invention can be formed by reduction of the hydrazine derivatives, as exemplified below.

C. Condensation of 2-Methoxy-3-Hydrazinyl Pyrazine with Substituted Aryl or Heteroaryl Aldehydes.

2-Methoxy-3-hydrazinyl pyrazine and a selected substituted aryl or heteroaryl aldehyde, in this instance 3,5-dichloro salicyl aldehyde, are dissolved in an ethereal solvent chosen from a group consisting of diethyl ether and tetrahydrofuran. To this is then added an organic acid, preferably acetic acid, and the mixture allowed to stir at ambient temperature for a period of 1–5 hrs, after which time the ethereal solvent, in this instance tetrahydrofuran, is removed in vacuo to afford a suspension of product in the organic acid, in this instance acetic acid. Water was then added to the suspension and the suspension was then filtered to give, in this instance, 3,5-dichloro-2-hydroxybenzaldehyde-N-(3-methoxy-2-pyrazinyl) hydrazone (1).

Monoalkyl derivatives of 2,4 dihydroxy benzaldehyde may be formed using the following procedure.

2,4-Dihydroxybenaldehyde is dissolved in a suitable amount of anhydrous acetonitrile, to which was added 325-mesh potassium carbonate (2.5 molar equivalents) and potassium iodide (0.2 molar equivalents) and benzyl halides, in this instances para-lauryl benzyl chloride. The reaction mixture was heated at reflux for 2 h. Upon cooling, the reaction mixture was partitioned between ethyl acetate and water. The aqueous layer was extracted with ethyl acetate. The combined organic layers were washed with brine and dried over sodium sulfate, and filtered. The solvent was removed in vacuo. The crude products were purified by column chromatography (ethyl acetate/hexane). 4-Substituted dihydroxybenzaldehyde, in this instance, the 4-(p-laurylbenzyl)-2-hydroxybenzaldehyde was isolated in 66% yield.

D. Reduction of 2-Hydroxy substituted benzaldehyde-N-(substituted aryl or heteroaryl)hydrazone to 2-Hydroxy substituted benzaldehyde-N-(substituted aryl or heteroaryl) hydrazine.

2-Hydroxy substituted benzaldehyde-N-(substituted aryl or heteroaryl)hydrazone, in this instance 2-Hydroxy benzaldehyde-N-3-(2-methoxypyrazinyl)hydrazone, are dissolved in a suitable amount of an alcoholic solvent, preferably ethanol, to which was added sodium cyanoborohydride (4.5 molar equivalents). The acidity of the reaction solution was adjusted to pH=4–6 with HCl solution in MeOH. The reaction mixture was then heated at 50° C. for a period of 30 min to 24 h, preferably 30 min. The reaction mixture was diluted with saturated sodium bicarbonate solution followed by extraction with ethyl acetate. The organic layer was dried over sodium sulfate. The solvent was removed in vacuo to yield a crude product which was further purified by column chromatography (ethyl acetate/hexane) to afford the desired product in 54% yield.

The following is a chemical process for the efficient production of N[substituted aryl or heteroaryl]-2-[(E)-(substituted aryl or heteroaryl)methylidene]-1-hydrazonecarbothioamides which are useful as antifungal agents.

E. Production of Substituted Aryl or Heteroaryl Aldehyde Hydrazones from Substituted Aryl or Heteroaryl Aldehydes.

A selected substituted aryl or heteroaryl aldehyde, in this instance 3,5-dichloro salicyl aldehyde, was dissolved in an alcoholic solvent, in this instance ethanol, and hydrazone added. The mixture was then heated to reflux and the alcoholic solvent distilled until a residue remained. The residue was then slurried with 10:1 hexane:ethyl acetate and filtered to afford the desired substituted aryl or heteroaryl aldehyde hydrazone, in this instance 3,5-dichloro salicyl aldehyde hydrazone.

F. Production of N-[Substituted Aryl or Heteroaryl]-2-[(E)-(Substituted Aryl or Heteroaryl)Methylidene]-1-

Hydrazonecarbothioamides from Substituted Aryl or Heteroaryl Aldehyde Hydrazones and Substituted Aryl or Heteroaryl Thioisocyanates.

A selected substituted aryl or heteroaryl aldehyde hydrazone, in this instance 3,5-dichloro salicyl aldehyde hydrazone, was dissolved in an alcoholic solvent, in this instance ethanol, and a selected substituted aryl or heteroaryl thioisocyanate, in this instance 3,5-bis trifluoromethyl phenyl thioisocyanate, added to the solution. The mixture was then heated at 60° C. for a period of 1–5 hrs, after which time the solvent was removed in vacuo and the residue slurried in 5:1 hexane: ethyl acetate and filtered to afford N-[substituted aryl or heteroaryl]-2[(E)-(substituted aryl or heteroaryl) methylidene]-1-hydrazonecarbothioamides, in this instance N-[3,5 bis(trifluoromethyl)phenyl]-2-[(E)-(3,5-dichloro-2-hydroxy phenyl)methylidene]-1-hydrazonecarbothioamide (35).

Pharmaceutical Formulations

The present invention provides pharmaceutical formulations comprising the aryl and heteroaryl hydrazone or thiourea derivatives disclosed herein in conjunction with a pharmaceutically acceptable carrier or diluent.

The formulations of the present invention can be solutions, suspensions, emulsions, syrups, elixirs, capsules, tablets, and the like. The compositions may contain a suitable carrier, diluent, or excipient, such as sterile water, physiological saline, glucose, or the like. Moreover, the formulations can also be lyophilized, and/or may contain auxiliary substances, such as wetting or emulsifying agents, pH buffering agents, adjuvants, gelling or viscosity enhancing additives, preservatives, flavoring agents, colors, and the like, depending upon the route of administration and the preparation desired. Standard texts, such as "Remington's Pharmaceutical Science", 17th Ed., 1985, incorporated herein by reference, may be consulted to prepare suitable preparations, without undue experimentation.

The formulations can include powdered carriers, such as lactose, sucrose, mannitol, starch, cellulose derivatives, magnesium stearate, stearic acid, and the like. Further, tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. The formulations can also contain coloring and flavoring to enhance patient acceptance.

In general, water, a suitable oil, saline, aqueous dextrose (glucose), and related sugar solutions and glycols such as propylene glycol or polyethylene glycols such as propylene glycol or polyethylene glycols are suitable carriers for parenteral solutions. Solutions for parenteral administration contain preferably a water soluble salt of the active ingredient, suitable stabilizing agents, and, if necessary, buffer substances.

Antioxidants such as, for example, sodium bisulfate, sodium sulfite, citric acid and its salts, sodium EDTA, ascorbic acid, and the like can be used either alone or in combination with other suitable antioxidants or stabilizing agents typically employed in the pharmaceutical compositions. In addition, parenteral solutions can contain preservatives, such as, for example, benzalkonium chloride, methyl- or propyl-paraben, chlorobutanol and the like.

The formulations can also include any of the commonly used disintegrants, lubricants, plasticizers, colorants, and dosing vehicles. Suitable pharmaceutical carriers are described in Remington's Pharmaceutical Sciences, A. Osol, a standard reference text in this field.

In order for a composition to be administered to an animal or human, and for any particular method of administration, it is preferred to determine the toxicity, such as by determining the MIC ("minimum inhibitory concentration") and MBC ("minimum bacteriocidal concentration") in a suitable animal model, e.g., a mouse; the dosage of the composition (s), and the concentration of components in the composition; and the timing of administration in order to maximize the antimicrobial response. Such factors can be determined without undue experimentation by such methods as titrations and analysis of sera for antibodies or antigens, e.g., by ELISA and/or EFFIT analysis. Such determinations do not require undue experimentation from the knowledge of the skilled artisan, the present disclosure and the documents cited herein.

Suitable formulations typically contain from about 1 to about 1000 mg of active ingredient per dosage unit. In these pharmaceutical compositions, the active ingredient will ordinarily be present in an amount of about 0.5 to about 95%, by weight, based on the total weight of the composition.

The magnitude of the therapeutic dose of the compounds of the invention will vary with the nature and severity of the condition to be treated and with the particular compound and its route of administration. In general, the daily dose range for antifungal activity lies in the range of 0.001 to 100 mg/kg of body weight in a mammal, preferably 0.001 to 25 mg/kg, and most preferably 0.001 to 1.0 mg/kg, in single or multiple doses. In unusual cases, it may be necessary to administer doses above 100 mg/kg.

Any suitable route of administration may be employed for providing a mammal, especially a human, with an effective dosage of a compound disclosed herein. For example, oral, rectal, topical, enteral, parenteral, ocular, pulmonary, nasal, etc., routes may be employed. Dosage forms include tablets, troches, dispersions, suspensions, solutions, capsules, creams, ointments, aerosols, etc.

The compositions include compositions suitable for oral, rectal, topical (including transdermal devices, aerosols, creams, ointments, lotions and dusting powders), parenteral (including subcutaneous, intramuscular and intravenous), ocular (ophthalmic), pulmonary (nasal or buccal inhalation) or nasal administration. Although the most suitable route in any given case will depend largely on the nature and severity of the condition being treated and on the nature of the active ingredient, the compositions of the invention may be conveniently presented in unit dosage form and prepared by any of the methods well known in the art of pharmacy.

As used herein, the term "treatment" with regard to an antifungal infection includes preventing, retarding, and/or reducing a disease, pathological condition or one or more symptoms thereof, in animals, particularly mammals, and most particularly humans. An antifungal effective amount is an amount that results in any improvement in one or more clinical or histological symptoms or diagnostic markers observed by a medical practitioner or determined by quantitative or semiquantitative techniques. Non-limiting examples of appropriate techniques include without limitation analysis of blood and urine. Any suitable assay may be used for determining antifungal effective amounts without undue experimentation, taking into account the route of administration and the age, sex, weight, species and condition of the particular patient.

Biological Examples

Compounds of the invention were tested for antifungal susceptibility using broth microdilution assay established by the National Committee for Clinical Laboratory Standards, in NCCLS Document M27-A, which is hereby incorporated by reference. Minimum inhibitory concentrations (MICs) and minimum fungicidal concentrations (MFCs) were measured.

Media

Sabouraud dextrose agar (SDA)

10 g Bacto Neopeptone 40 g Bacto Dextrose 15 g Bacto Agar

Suspend contents in 1 liter of water and boil while stirring to dissolve completely. Autoclave for 15 minutes. SDA is sold as a powdered mix by DIFCO (Cat #0109-17-1).

Potato dextrose agar (PDA)

4 g Potato extract 20 g Bacto Dextrose 15 g Bacto Agar

Suspend contents in 1 liter of water and boil while stirring to dissolve completely. Autoclave for 15 minutes. PDA is sold as a powdered mix by DIFCO (Cat #0013-17-6).

RPMI-1640

10.4 g powdered media (Sigma R-6504, with glutamine and without bicarbonate)

2.0 g $NaHCO_3$ (Sigma S-6297)

34.53 g MOPS buffer (Sigma M-6270)

Dissolve powdered media and $NaHCO_3$ in 900 ml distilled water. Add MOPS and stir until dissolved. Adjust pH to 7.0 using 1N NaOH. Bring final volume to 1 liter, filter sterilize, and store at 4° C.

RMPI-1640 with 12.5% mouse serum 10.4 g powdered media (Sigma R-6504, with glutamine and without bicarbonate)

2.0 g $NaHCO_3$ (Sigma S-6297)

34.53 g MOPS buffer (Sigma M-6270)

50 ml mouse serum (Sigma S-7273)

Dissolve powdered media and $NaHCO_3$ in 750 ml distilled water. Add MOPS and stir until dissolved. Adjust pH to 7.0 using 1N NaOH and bring volume to 875 ml. Remove 350 ml and add to it 50 ml of mouse serum. Bring remaining volume of media (525 ml) to 600 ml with the addition of 75 ml of distilled water. Filter sterilize each solution and store at 4° C.

Inoculum Preparation

Yeasts

Yeasts (*Saccharomyces cerevisiae* and *Candida albicans*) are cultured on SDA plates in a 35° C. incubator. Strains on SDA plates are stored at 4° C. and used as working stock cultures.

Inoculum for susceptibility testing is prepared from fresh 24 hour cultures. 5–10 colonies are scraped from the plate and suspended in three milliliters of sterile 0.85% saline (8.5 g/liter NaCl). The cell density of the solution is determined by measuring the absorbance in a spectrophotometer (Shimadzu UV-1201S UV-VIS Spectrophotometer) set at 600 nm. An absorbance value between 0.1 and 0.4 is required for an accurate reading.

For *Candida albicans* strains ATCC 10231, 1.0 $OD_{600}$ unit is approximately $10^7$ cells per ml. For *Saccharomyces cerevisiae* strain CTY552, 1.0 $OD_{600}$ unit is slightly less than $10^7$ cells per ml. Cell suspensions are diluted with the appropriate medium (typically RPMI-1640) to $OD_{600}$=0.0003 for Candida and $OD_{600}$=0.0004 for Saccharomyces. The diluted suspension contains approximately $3 \times 10^3$ cells per ml (this is a 2×concentration inoculum). Two 100 μl aliquots of this dilution are spread on SDA plates and incubated at 35° C. for 1–2 days to determine the precise number of colony forming units. An acceptable range for the inoculum (2×) is $1-5 \times 10^3$ cfu/ml (100–500 for 100 μl). Following two-fold dilution of the inoculum with compound, the final concentration of cells will be $0.5-2.5 \times 10^3$ per ml. The inoculum is kept at 4° C. and used within a few hours.

Filamentous fungi

Filamentous fungi (*Aspergillus* spp.) is cultured on PDA plates in a 35° C. incubator. Inoculum of Aspergillus for susceptibility testing is prepared from plates incubated at 35° C. for 5 days. Colonies are covered with 5 ml of sterile 0.85% saline (8.5 g/liter NaCl) and gently rocked for 10–15 minutes. To dislodge the conidia, an automatic pipettor is used to gently wash over the colonies. The saline solution is removed from the plate and the heavy particles are allowed to settle for 3–5 minutes. The upper suspension is removed and vortexed for 15 sec. The turbidity of the solution is determined by measuring the absorbance in a spectrophotometer (Shimadzu UV-1201S UV-VIS Spectrophotometer) set at 600 nm. An absorbance value between 0.1 and 0.4 is required for an accurate reading.

The cell suspension is diluted with the appropriate medium (typically RPMI-1640) to $OD_{600}$=0.0004. The final suspension should contain approximately $3 \times 10^3$ cfu per ml (this is a 2×concentration inoculum). Two 100 μl aliquots of this dilution are spread on SDA plates and incubated at 35° C. for 1–2 days to determine the precise number of colony forming units. An acceptable range for the inoculum (2×) is $1-5 \times 10^3$ cfu/ml (100–500 for 100 μl). Following two-fold dilution of the inoculum with compound, the final concentration of cells will be $0.5-2.5 \times 10^3$ per ml. The inoculum is kept at 4° C. and used within a few hours.

Compound Preparation

Stock solutions and concentrations tested will vary from compound to compound. In general, though, stock solutions of 12.8 mg/ml in DMSO (Sigma D-8779) are prepared. This will allow for a 128 μg/ml starting test concentration containing 1% DMSO. Stock solutions are stored at −20° C. and dilutions for antifungal testing are freshly prepared before each assay.

For compounds of unknown activity or ones with MIC values of >4 μg/ml, a range of concentrations from 128 μg/ml to 0.125 μg/ml are used. More active compounds, such as Amphotericin B (Sigma A2411) and Itraconazole (Research Diagnostics Inc. cat#30.211.44), require a lower range of concentrations (16 μg/ml to 0.016 μg/ml). Stock solutions of Amphotericin B and Itraconazole are prepared at 1.6 mg/ml in DMSO. Amphotericin B is sold as a powder that is approximately 80% Amphotericin B. Stock solutions are made accordingly (2.0 mg of powder for a 1 ml solution of 1.6 mg/ml Amphotericin B).

Stock solutions of control compounds (1.6 mg/ml, Amphotericin B or Itraconazole) are initially diluted in medium to a concentration of 32 μg/ml while stock solutions of test compounds (typically 12.8 mg/ml) are diluted to 256 μg/ml. Both of these (control and test compounds) represent 1:50 dilutions. For an assay with three fungal strains, 40 microliters of a stock solution are diluted to 2.0 ml with room temperature medium.

Assay Setup

Antifungal susceptibility tests are setup in polystyrene, 96-well, flat bottom plates (Costar 9017). To every well in columns 2–12 is added 100 microliters of media. An electronic multichannel (12) pipettor with no tip on channel one is used. To every well in column one is added 200 microliters of diluted compound (32 µg/ml for Amphotericin B and Itraconazole controls, 256 µg/ml for test compounds, 100-fold dilution for natural product extracts). A manual multichannel (8) pipettor is then used to set up a series of 2-fold dilutions. 100 microliters is removed from each well of column one and mixed with 100 microliters in column 2. This is done successively (column two to column three etc.) to produce a set of 11 serial dilutions (column 12 is a drug free control).

To every well in two rows, 100 µl of inoculum (2x) of a single strain is added. To the final two rows on the plate (G & H), only media is added. Addition of inoculum is best accomplished using an electronic multichannel (12) pipettor. This setup (see below) creates a starting cell density of 500–2500 per µg/ml (100–500 per well) and drug concentration ranging from 16 µg/ml to 0.016 µg/ml for controls (Amphotericin B and Itraconazole), 128 µg/ml to 0.125 µg/ml for pure test compounds, and 200 to 204, 800-fold dilutions for natural product extracts. Two 100 µl aliquots of each inoculum (2x) are spread on SDA plates and incubated at 35° C. for 1–2 days to determine the precise number of colony forming units. An acceptable range for the inoculum (2x) is 1–5×10$^3$ cfu/ml (100–500 for 100 µl). Following two-fold dilution of the inoculum with compound, the final concentration of cells will be 0.5–2.5×10$^3$ per ml.

The plates should then be placed in a dark, 35° C. incubator for 48 hours.

Minimum Inhibitory Concentration (MIC)

The MIC is the lowest concentration of an antifungal agent that inhibits growth of the organism. For Amphotericin B, the lowest drug concentration which gives no visible growth is the MIC. For Itraconazole (and other azoles), the lowest drug concentration which reduces growth to ≦20% of the growth control (column 12) is the MIC.

For test compounds that give a sharp endpoint (like Amphotericin B), the lowest drug concentration which gives no visible growth is the MIC. For test compounds that give a trailing effect on inhibition of cell growth (like the azoles), the lowest drug concentration which reduces growth to ≦20% of the growth control (as determined by measurement of turbidity) is the MIC.

The turbidity of each well is determined by measuring the absorbance at 415 nm on a plate reader (BIO-RAD Model 3550-UV).

The following Table 1 contains the results of MIC testing of compounds of the invention.

TABLE I

| Compound | MIC (µg/ml) | | |
|---|---|---|---|
| | C. albicans | S. serevisiae | A. Nidulans |
| (1) | 1 | 1 | 2 |
| (2) | 1 | 1 | 2 |
| (3) | 0.5 | 1 | 2 |
| (4) | 1 | 1 | 2 |
| (5) | 1 | 1 | 2 |
| (6) | 2 | 1 | 1 |
| (7) | 1 | 1 | 2 |
| (8) | 4 | 2 | >128 |
| (9) | 8 | 8 | 16 |
| (10) | 2 | 1 | 2 |
| (11) | 2 | 1 | 2 |
| (12) | 4 | 4 | 8 |
| (13) | 1 | 0.5 | 4 |

TABLE I-continued

| Compound | MIC (µg/ml) | | |
|---|---|---|---|
| | C. albicans | S. serevisiae | A. Nidulans |
| (12) | 0.5 | 0.5 | 1 |
| (15) | 1 | 1 | 8 |
| (16) | 8 | 8 | 128 |
| (17) | >128 | >128 | >128 |
| (18) | 1 | 1 | 0.125 |
| (19) | 1 | 1 | 0.125 |
| (20) | 8 | 16 | 2 |
| (21) | 2 | 1 | 1 |
| (22) | >64 | >64 | >64 |
| (23) | 2 | 2 | 0.125 |
| (24) | 0.25 | 0.5 | 0.063 |
| (25) | 2 | 2 | 1 |
| (26) | 2 | 1 | 0.5 |
| (27) | 1 | 1 | 0.25 |
| (28) | 1 | 1 | 0.25 |
| (29) | 1 | 1 | 1 |
| (30) | 2 | 1 | 0.5 |
| (35) | 2 | 2 | 4 |
| (36) | 16 | 2 | >128 |
| (37) | 0.5 | 1 | 1 |
| (38) | 2 | 2 | 4 |
| (39) | 2 | 2 | 4 |
| (40) | 32 | 2 | >128 |
| (41) | >128 | >128 | >128 |
| (42) | 0.25 | 0.25 | 0.25 |
| (43) | 0.5 | 0.5 | 0.25 |
| (44) | 8 | 2 | 2 |
| (45) | 1 | 0.5 | 0.5 |
| (46) | 1 | 0.25 | 0.25 |
| (47) | 2 | 1 | 0.5 |
| (48) | 1 | 0.5 | 0.5 |
| (49) | 2 | 1 | 0.5 |
| (50) | 1 | 0.5 | 0.5 |
| (51) | 16 | 0.5 | 1 |
| (52) | >64 | | >64 |
| (32) | 1 | 2 | 0.125 |
| (33) | 2 | 1 | 4 |
| (34) | 2 | 1 | 1 |

Minimum Fungicidal Concentration (MFC)

The MFC is the lowest concentration of an antifungal agent that results in an inviable culture. Two slightly different standards and assays are applied, depending on the circumstances. For each of the two methods, though, culture viability should be determined beginning with the drug dilution immediately below the MIC and continuing through to the highest drug concentration.

The first and more rigorous standard considers a culture to be inviable if it contains ≦1% of the colony forming units of the starting culture. This is determined by completely removing the cells from a well of the microtiter plate and placing them in a microfuge tube containing 1.3 ml of RPMI media. The cells are spun for 2 minutes, supernatant poured off, cells resuspended in the remaining media, and spread on an SDA plate. The plate is incubated at 35° C. for 1–2 days, and the colonies counted. These numbers are compared to the original cfu count from day 1 of the assay.

A second, simpler method is more practical for processing a large number of samples. Following resuspension of the cells by pipetting, 15 microliters is spotted directly to an SDA plate and incubated for 2 days at 35° C. A culture is considered inviable if no colonies form on the plate.

TABLE II

| | |
|---|---|
| MFC (mg/ml) of C. albicans, S. servisa and A. nidulans | |
| Compound | MFC (μg/ml) C. albicans |
| (1) | >128 |
| (2) | >128 |
| (3) | >128 |
| (4) | >128 |
| (10) | >128 |
| (11) | >128 |
| (12) | >128 |
| (13) | >128 |
| (14) | >128 |
| (15) | >128 |
| (16) | >128 |
| (17) | ND |
| (35) | >128 |
| (37) | ND |
| (41) | ND |
| (42) | >128 |
| (48) | >128 |
| (49) | >128 |

The following Table 3 contains the results of $IC_{50}$ testing of compounds of the invention.

TABLE III

| | |
|---|---|
| $IC_{50}$ (μg/ml) of | |
| Compound | $IC_{50}$ (μg/ml) |
| (1) | 20 |
| (16) | 160 |
| (35) | 160 |

All patent applications, patents, patent publications, and literature references cited in this specification are hereby incorporated by reference in their entirety. In the case of inconsistencies, the present description, including definitions, is intended to control. Accordingly, the above description should be construed as illustrating and not limiting the scope of the invention. All such obvious changes and modifications are within the patented scope of the appended claims.

We claim:

1. A compound of formula (I)

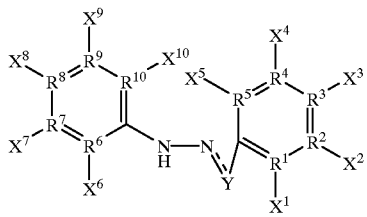

wherein
Y is CH when the dotted line leading from Y to N is present and represents a bond, or $CH_2$ when the dotted line leading from Y to N is absent;
$R^1$, $R^2$, $R^3$, $R^4$ and $R^5$ are carbon;
$X^1$ is selected from the group consisting of ZH, where Z is O or S, or $NR^{21}R^{22}$, wherein $R^{21}$ and $R^{22}$ are independently selected from the group consisting of hydrogen, alkyl or acyl;
$X^2$, $X^3$, $X^4$ and $X^5$ are independently selected from the group consisting of hydrogen, halogen, hydroxyl, alkyl, alkenyl, alkynyl, acyl, alkoxy, alkenyloxy, alkynyloxy, acyloxy, cyano, trifluoromethyl, nitro, aryl, heteroaryl, a non-aromatic heterocyclic group, a fused or polycyclic ring structure, N-alkyl amino, N-alkenyl amino, N-alkynyl amino, N-acyl amino, N,N-alkyl amino, N,N-alkenyl amino, N,N-alkynyl amino, N,N-acyl amino, thio, sulfonamide, and $SO_2$; or are independently selected from the group consisting of
(a) $C(O)NHQ^1Q^2$, wherein $Q^1$ is $C_{1-3}$ alkyl and $Q^2$ is aryl, heteroaryl or a non-aromatic heterocyclic group, wherein said aryl, heteroaryl or non-aromatic heterocyclic group is optionally substituted with hydroxyl, alkyl, alkoxy, carboxyl, or acyl; or
(b) $C(O)Q^3$, wherein $Q^3$ is selected from the group consisting of hydrogen, OH, O—$C_{1-3}$ alkyl; or
(c) $SO_2Q^4$, wherein $Q^4$ is aryl, heteroaryl or non-aromatic heterocyclic, wherein said aryl, heteroaryl or non-aromatic heterocyclic is optionally substituted with hydroxyl, alkyl, alkoxy, carboxyl or acyl; or
(d) $OQ^5Q^6$, wherein $Q^5$ is $C_{1-3}$ alkyl and $Q^6$ is aryl, heteroaryl or a non-aromatic heterocyclic group, wherein said aryl, heteroaryl or non-aromatic heterocyclic group is optionally substituted with hydroxyl, allyl, alkoxy, carboxyl, or acyl;
$R^6$ and $R^9$ are nitrogen;
$R^7$, $R^8$ and $R^{10}$ are carbon;
$X^6$ and $X^9$ are absent;
$X^7$, $X^8$ and $X^{10}$ are independently selected from the group consisting of hydrogen, halogen, hydroxyl, alkyl, alkenyl, alkynyl, acyl, alkoxy, alkenyloxy, alkynyloxy, acyloxy, cyano, trifluoromethyl, nitro, aryl, heteroaryl, a non-aromatic heterocyclic group, a fused or polycyclic ring structure, N-alkyl amino, N-alkenyl amino, N-alkynyl amino, N-acyl amino, N,N-alkyl amino, N,N-alkenyl amino, N,N-alkynyl amino, N,N-acyl amino, thio, sulfonamide, and sulfonyl; or are independently selected from the group consisting of
(a) $C(O)NHQ^1Q^2$, wherein $Q^1$ is $C_{1-3}$ alkyl and $Q^2$ is aryl, heteroaryl or non-aromatic heterocyclic group, wherein said aryl, heteroaryl or non-aromatic heterocyclic group is optionally substituted with hydroxyl, alkyl, alkoxy, carboxyl, or acyl; or
(b) $C(O)Q^3$, wherein $Q^3$ is selected from the group consisting of hydrogen, OH, O—$C_{1-3}$ alkyl; or
(c) $SO_2Q^4$, wherein $Q^4$ is aryl, heteroaryl or non-aromatic heterocyclic, wherein said aryl, heteroaryl or non-aromatic heterocyclic is optionally substituted with hydroxyl, alkyl, alkoxy, carboxyl or acyl; or
(d) $OQ^5Q^6$, wherein $Q^5$ is $C_{1-3}$ alkyl and $Q^6$ is aryl, heteroaryl or a non-aromatic heterocyclic group, wherein said aryl, heteroaryl or non-aromatic heterocyclic group is optionally substituted with hydroxyl, alkyl, alkoxy, carboxyl, or acyl;

or a pharmaceutically acceptable salt thereof.

2. A compound of claim 1 wherein $X^1$ is OH.

3. A compound of claim 2 wherein $R^4$ is C and $X^4$ is COOH.

4. A compound of claim 3 wherein one of $X^6$ to $X^{10}$ is selected from the group consisting of $OCF_3$, $C_{1-4}$ alkyl, $C_{1-4}$ alkoxy, COOH or halogen.

5. The compound of claim 1 wherein $X^{10}$ is $C_{1-4}$ alkoxy.

6. A compound of claim 2 wherein the dotted line leading from N to Y is present and Y is CH.

7. A compound of claim 2 wherein the dotted line leading from N to Y is absent and Y is $CH_2$.

8. The compound of claim 1 which is selected from the group consisting of 3,5-dichloro-2-hydroxybenzaldehyde-N-(3-methoxy-2-pyrazinyl)hydrazone;
5-chloro-2-hydroxybenzaldehyde-N-(3-methoxy-2-pyrazinyl)hydrazone;
3-fluoro-2-hydroxybenzaldehyde-N-(3-methoxy-2-pyrazinyl)hydrazone;
2-hydroxybenzaldehyde-N-(3-methoxy-2-pyrazinyl) hydrazone;
4,6-dimethoxy-2-hydroxybenzaldehyde-N-(3-methoxy-2-pyrazinyl)hydrazone;
2,3-dihydroxybenzaldehyde-N-(3-methoxy-2-pyrazinyl) hydrazone;
2,4-dihydroxybenzaldehyde-N-(3-methoxy-2-pyrazinyl) hydrazone;
2,3,4-trihydroxybenzaldehyde-N-(3-methoxy-2-pyrazinyl) hydrazone;
2-quinolinecarbaldehyde N-(3-methoxy-2-pyrazinyl) hydrazone;
2-pyridinecarbaldehyde-N-(3-methoxy-2-pyrazinyl) hydrazone;
3-ethoxy-2-hydroxybenzaldehyde-N-(3-methoxy-2-pyrazinyl)hydrazone;
2-hydroxy-3-nitrobenzaldehyde-N-(3-methoxy-2-pyrazinyl)hydrazone;
2-hydroxy-4-methoxybenzaldehyde-N-(3-methoxy-2-pyrazinyl)hydrazone;
5-bromo-2-hydroxy-3-methoxybenzaldehyde-N-(3-methoxy-2-pyrazinyl)hydrazone;
6-bromo-2-hydroxy-3-methoxybenzaldehyde-N-(3-methoxy-2-pyrazinyl)hydrazone;
3,5-dichloro-2-hydroxybenzaldehyde-N-(3-chloro-2-pyrazinyl)hydrazine;
3-carboxyl-2-hydroxybenzaldehyde-N-(3-methoxy-2-phenyl)hydrazine;
5-carboxyl-2-hydroxybenzaldehyde-N-phenyl hydrazone;
2-hydroxybenzaldehyde-N-phenyl hydrazone;
5-carboxyl-2-hydroxybenzaldehyde-N-3-nitro-phenyl hydrazone;
5-carboxyl-2-hydroxybenzaldehyde-N-2-trifluoromethyloxy-phenyl hydrazone;
5-carboxyl-2-hydroxybenzaldehyde-N-2-carboxyl-phenyl hydrazone;
5-carboxyl-2-hydroxybenzaldehyde-N-3-fluorophenyl hydrazone;
5-carboxyl-2-hydroxybenzaldehyde-N-2-fluoro-phenyl hydrazone;
5-carboxyl-2-hydroxybenzaldehyde-N-2-bromophenyl hydrazone;
5-carboxyl-2-hydroxybenzaldehyde-N-2-chlorophenyl hydrazone;
5-carboxyl-2-hydroxybenzaldehyde-N-3-methyl-phenyl hydrazone;
5-carboxyl-2-hydroxybenzaldehyde-N-2-methoxy-phenyl hydrazone;
5-carboxyl-2-hydroxybenzaldehyde-N-3-chloro-2-methyl-phenyl hydrazone;
5-carboxyl-2-hydroxybenzaldehyde-N-3-chloro-phenyl hydrazone;
2-hydroxybenzaldehyde-N-phenyl hydrazine;
2-hydroxybenzaldehyde-N-(3-methoxy-2-pyrazinyl) hydrazine; and
2-pyridyl-benzaldehyde-N-(3-methoxy-2-pyrazinyl) hydrazine;

9. A method for inhibiting fungal replication comprising contacting a microorganism with an effective amount of a compound of claim 1.

10. A method for preventing or treating fungal infections in an animal comprising administering to an animal in need thereof an effective amount of a compound of claim 1.

11. A pharmaceutical formulation comprising a compound of claim 1.

* * * * *